(12) United States Patent
Barror et al.

(10) Patent No.: US 8,626,310 B2
(45) Date of Patent: Jan. 7, 2014

(54) EXTERNAL RF TELEMETRY MODULE FOR IMPLANTABLE MEDICAL DEVICES

(75) Inventors: Michael William Barror, Gilbert, AZ (US); William D. Verhoef, Andover, MN (US); Joyce K. Yamamoto, Maple Grove, MN (US); Robert S. Wentink, Lino Lakes, MN (US); Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 543 days.

(21) Appl. No.: 12/347,540

(22) Filed: Dec. 31, 2008

(65) Prior Publication Data
US 2010/0168818 A1 Jul. 1, 2010

(51) Int. Cl.
*A61N 1/08* (2006.01)

(52) U.S. Cl.
USPC .............................. 607/60; 607/36

(58) Field of Classification Search
USPC ...................... 607/32, 36, 60, 156
See application file for complete search history.

(56) References Cited

U.S. PATENT DOCUMENTS

| | | | |
|---|---|---|---|
| 5,023,624 A | 6/1991 | Heckaman et al. | |
| 5,198,824 A | 3/1993 | Poradish | |
| 5,203,345 A * | 4/1993 | Kennedy et al. | 600/549 |
| 5,219,377 A | 6/1993 | Poradish | |
| 5,387,888 A | 2/1995 | Eda et al. | |
| 5,456,698 A * | 10/1995 | Byland et al. | 607/36 |
| 5,620,476 A | 4/1997 | Truex et al. | |
| 6,107,227 A | 8/2000 | Jacquin et al. | |
| 6,320,547 B1 | 11/2001 | Fathy et al. | |
| 6,379,300 B1 | 4/2002 | Haubrich | |
| 6,391,082 B1 | 5/2002 | Holl | |
| 6,414,835 B1 | 7/2002 | Wolf et al. | |
| 6,505,072 B1 | 1/2003 | Linder et al. | |
| 6,556,169 B1 | 4/2003 | Fukuura et al. | |
| 6,580,402 B2 | 6/2003 | Navarro et al. | |

(Continued)

FOREIGN PATENT DOCUMENTS

| | | |
|---|---|---|
| EP | 1362614 A1 | 11/2003 |
| WO | WO/01/02468 | 1/2001 |

OTHER PUBLICATIONS (PCT/US2009/068908) PCT Notification of Transmittal of the International Search Report and the Written Opinion of the International Searching Authority, 13 pages.

(Continued)

*Primary Examiner* — Carl H Layno
*Assistant Examiner* — Erica Lee
(74) *Attorney, Agent, or Firm* — Stephen W. Bauer; Michael J. Ostrom (57) ABSTRACT

An implantable medical device ("IMD") is provided having an antenna and an RF telemetry module for far field telemetry communications arranged on an exterior of the IMD housing, such that telemetry signal processing may be performed on the exterior of the housing. One or more feedthrough conductive paths extend through the housing to communicatively couple the RF module to circuitry within the housing. In this manner RF module is arranged entirely external to the housing, such that only power and/or low frequency data bit signals are required to be passed through the feedthrough conductive path. This allows the feedthrough conductive path to be filtered to prevent undesired interference signals (e.g., electromagnetic interference (EMI) signals) from entering the housing through the feedthrough conductive path coupled to the RF module. In some embodiments, the antenna and RF module are formed in an integrated assembly attachable to an exterior portion of the housing.

8 Claims, 6 Drawing Sheets

(56) References Cited

U.S. PATENT DOCUMENTS

| | | |
|---|---|---|
| 7,012,327 B2 | 3/2006 | Huff et al. |
| 7,122,891 B2 | 10/2006 | Dishongh et al. |
| 7,164,572 B1 | 1/2007 | Burdon et al. |
| 7,289,063 B2 | 10/2007 | Zaghloul |
| 7,317,946 B2 | 1/2008 | Twetan et al. |
| 7,392,015 B1 | 6/2008 | Farlow et al. |
| 2003/0083719 A1 | 5/2003 | Shankar et al. |
| 2003/0135246 A1* | 7/2003 | Mass et al. .............. 607/60 |
| 2004/0176811 A1 | 9/2004 | Von Arx et al. |
| 2005/0134520 A1 | 6/2005 | Rawat et al. |
| 2006/0212096 A1 | 9/2006 | Stevenson |
| 2006/0214855 A1 | 9/2006 | Harada et al. |
| 2006/0247712 A1 | 11/2006 | Fuller et al. |
| 2007/0200706 A1 | 8/2007 | Lee |
| 2007/0236861 A1 | 10/2007 | Burdon et al. |
| 2008/0021522 A1 | 1/2008 | Verhoef et al. |
| 2008/0288028 A1* | 11/2008 | Larson et al. .............. 607/60 |
| 2010/0114225 A1* | 5/2010 | Imran et al. .............. 607/9 |
| 2010/0161002 A1* | 6/2010 | Aghassian et al. ........ 607/60 |

OTHER PUBLICATIONS

Caiazzo, et al., A Metamaterial Surface for Compact Cavity Resonators, IEEE AP Letters, 2004, pp. 261-264, vol. 3.

Wu, et al., A study Using Metamaterials As Antenna Substrate to Enhance Gain, PIER 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-Forming and Direction-of-Arrival Considerations, Proceedings of the IEEE, Aug. 1997, pp. 1195-1245, vol. 85, No. 8.

* cited by examiner

EXTERNAL RF TELEMETRY MODULE FOR IMPLANTABLE MEDICAL DEVICES

TECHNICAL FIELD

The present invention relates generally to implantable medical devices (IMDs) and, more particularly, the present invention relates to external RF telemetry module configurations suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric, non-conductive polymer. The header block includes a mounting surface that conforms to, and is mechanically affixed against, a mating sidewall surface of the housing.

It has become common to provide a communication link between the electronic circuitry hermetically sealed within the can of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver. Generally, the IMD antenna is disposed within the hermetically sealed housing. However, the typically conductive housing can limit the radiation efficiency of the IMD RF telemetry antenna, thereby traditionally limiting the data transfer distance between the programmer head and the IMD RF telemetry antennas to a few inches. This type of system may be referred to as a "near field" telemetry system. In order to provide for "far field" telemetry, or telemetry over distances of a few to many meters from an IMD or even greater distances, attempts have been made to provide antennas outside of the hermetically sealed housing and within the header block. Many of such attempts of positioning an RF telemetry antenna outside of the hermetically sealed housing and in the header block have utilized wire antennas or planar, serpentine antennas, such as the antennas described in U.S. Pat. No. 7,317,946, which is hereby incorporated by reference in its entirety. However, the positioning of the antenna in the header block outside of the can has conventionally required the antenna to be connected to RF telemetry circuitry contained within the IMD through electrical feedthroughs that extend through the hermetically sealed can. Given the frequency, nature, and characteristics of the RF telemetry signals that are required to be transmitted from the antenna to the telemetry circuitry, the electrical feedthrough path for such telemetry signals can not typically be filtered, thereby leaving an open pathway for electromagnetic interference (EMI) signals or other types of interference signals to travel into the hermetically sealed can and negatively impact the circuitry contained within the IMD.

SUMMARY

In one or more embodiments, an implantable medical device ("IMD") is provided having an antenna and an RF telemetry module for far field telemetry communications arranged on an exterior of a housing for the IMD. The RF telemetry module and antenna are communicatively coupled together on the exterior of the housing. One or more feedthrough conductive paths extending through the housing to communicatively couple the RF telemetry module to at least one component within the housing. In this manner, the RF telemetry module and antenna are arranged entirely external to the housing to allow telemetry signal processing to occur outside of the housing, such that in some embodiments only power and/or low frequency data bit signals corresponding to radio frequency (RF) telemetry signals are passed through the feedthrough conductive path. This allows the feedthrough conductive path to be filtered to prevent undesired interference signals (e.g., electromagnetic interference (EMI) signals, magnetic resonance imaging (MRI) signals, etc.) from entering the housing through the feedthrough conductive path coupled to the RF telemetry module. In some embodiments, the antenna and RF telemetry module are formed in an integrated antenna and RF telemetry module that is attachable to an exterior portion of the housing.

In one or more embodiments, the RF telemetry module may be conformally shaped to a corresponding external region of the housing. A hermetic cover may be arranged over the RF telemetry module and sealed against an exterior surface of the housing so as to enclose the telemetry module and protect the RF telemetry module from the environment surrounding the implant location of the IMD. In some embodiments, the hermetic cover may comprise a connection header or header block. In one or more embodiments, a recessed region or shelf region may be within a portion of the exterior surface of the housing, such that the RF telemetry module may be arranged to be received within the recessed region on the exterior of the housing. The hermetic cover may then be arranged over the recessed region and sealed against the exterior surface of the housing so as to enclose the RF telemetry module within the recessed region. In one or more embodiments in which the antenna and RF telemetry module are formed as an integrated antenna and telemetry module assembly, one side of the integrated assembly may include the RF telemetry module attached thereto that is situated within the recessed region while the other side of the integrated antenna and telemetry module assembly serves as the hermetic cover that can serve to enclose the RF telemetry module within the recessed region.

In one or more embodiments, the integrated antenna and telemetry module assembly for the IMD may include a ceramic material such that the antenna is embedded within the ceramic material and the telemetry module may be attached to a portion of the ceramic material. In some embodiments, the ceramic material and antenna may be cofired together into a monolithic structure to which the RF telemetry module is attached. Since the RF telemetry module is located on the exterior of the housing, the RF telemetry module may be at least partially covered with a shielding layer for providing electromagnetic interference (EMI) and/or electromagnetic capability (EMC) isolation for the RF telemetry module from interference signals. In some embodiments, the RF telemetry module may comprise a potted external flex radio frequency (RF) module having self-contained RF circuitry and digital circuitry.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description may refer to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, an IMD having an improved antenna structure is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a signal (e.g., a UHF signal or the like) that can be processed by the IMD transceiver into commands and data that are intelligible to the IMD electronic operating system; and to convert the uplink telemetry signals (e.g., a UHF signal or the like) of the IMD transceiver electronics into electromagnetic power propagated through the body tissue and the atmosphere so that the EMD telemetry antenna or antennas can receive the signals.

Figure 1:
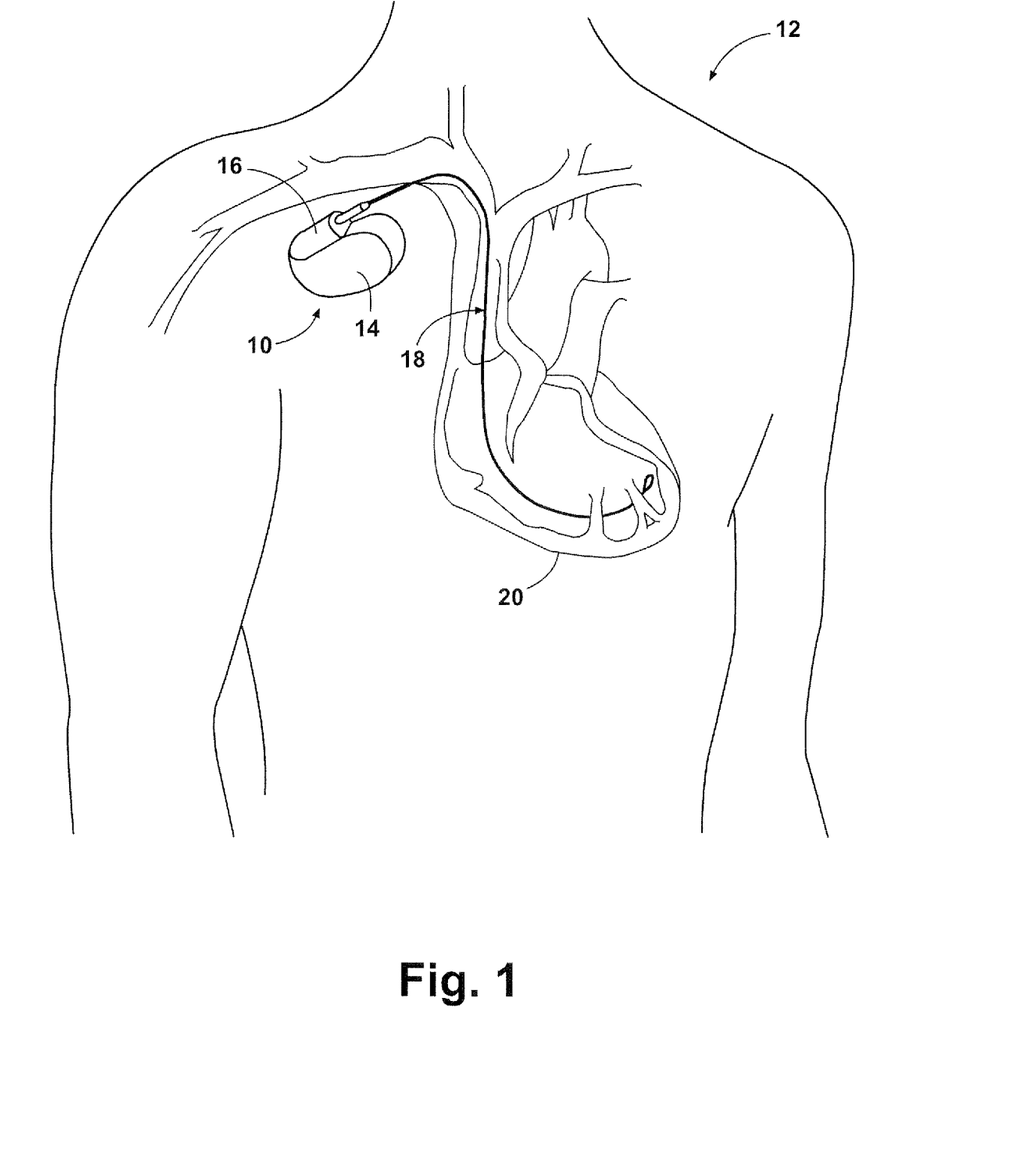
FIG. 1 illustrates an implantable medical device implanted in a human body in accordance with one or more embodiments of the present disclosure.

FIG. 1 is a perspective view of an IMD 10 implanted within a human body 12 in which one or more embodiments of the invention may be implemented. IMD 10 comprises a hermetically sealed housing 14 (or "can") and connector header or block module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions in a manner well known in the art. For example, such leads may enter at an end of header block 16 and be physically and electrically connected to conductive receptacles, terminals, or other conductive features located within header block 16. IMD 10 may be adapted to be implanted subcutaneously in the body of a patient such that it becomes encased within body tissue and fluids, which may include epidermal layers, subcutaneous fat layers, and/or muscle layers. While IMD 10 is depicted in FIG. 1 in an ICD configuration, it is understood that this is for purposes of illustration only and IMD 10 may comprise any type of medical device requiring a telemetry antenna.

In some embodiments, hermetically sealed housing 14 is generally circular, elliptical, prismatic, or rectilinear, with substantially planar major sides joined by perimeter sidewalls. Housing 14 is typically formed from pieces of a thin-walled biocompatible metal such as titanium. Two half sections of housing 12 may be laser seam welded together using conventional techniques to form a seam extending around the perimeter sidewalls. Housing 14 and header block 16 are often manufactured as two separate assemblies that are subsequently physically and electrically coupled together. Housing 14 may contain a number of functional elements, components, and features, including (without limitation): a battery; a high voltage output capacitor; integrated circuit ("IC") devices; a processor; memory elements; a therapy module or circuitry, etc. These components may be assembled in spacers and disposed within the interior cavity of housing 14 prior to seam welding of the housing halves. During the manufacturing process, electrical connections are established between components located within housing 14 and elements located within header block 16. For example, housing 14 and header block 16 may be suitably configured with IC connector pads, terminals, feedthrough elements, and other features for establishing electrical connections between the internal therapy module and the therapy lead connectors within header block 16 and for establishing connections between an external RF telemetry module and power or other components on the interior of the housing 14. Structures and techniques for establishing such electrical (and physical) feedthrough connections are known to those skilled in the art and, therefore, will not be described in detail herein. For example, U.S. Pat. No. 6,414,835 describes a capacitive filtered feedthrough array for an implantable medical device, the contents of which are hereby incorporated by reference.

In some embodiments, header block 16 may be formed from a suitable dielectric material, such as a biocompatible synthetic polymer. In some embodiments, the dielectric material of header block 16 may be selected to enable the passage of RF energy that is either radiated or received by a telemetry antenna (not shown in FIG. 1) encapsulated within header block 16. The specific material for header block 16 may be chosen in response to the intended application of IMD 10, the electrical characteristics of the environment surrounding the implant location, the desired operating frequency range, the desired RF antenna range, and other practical considerations.

Figure 2:
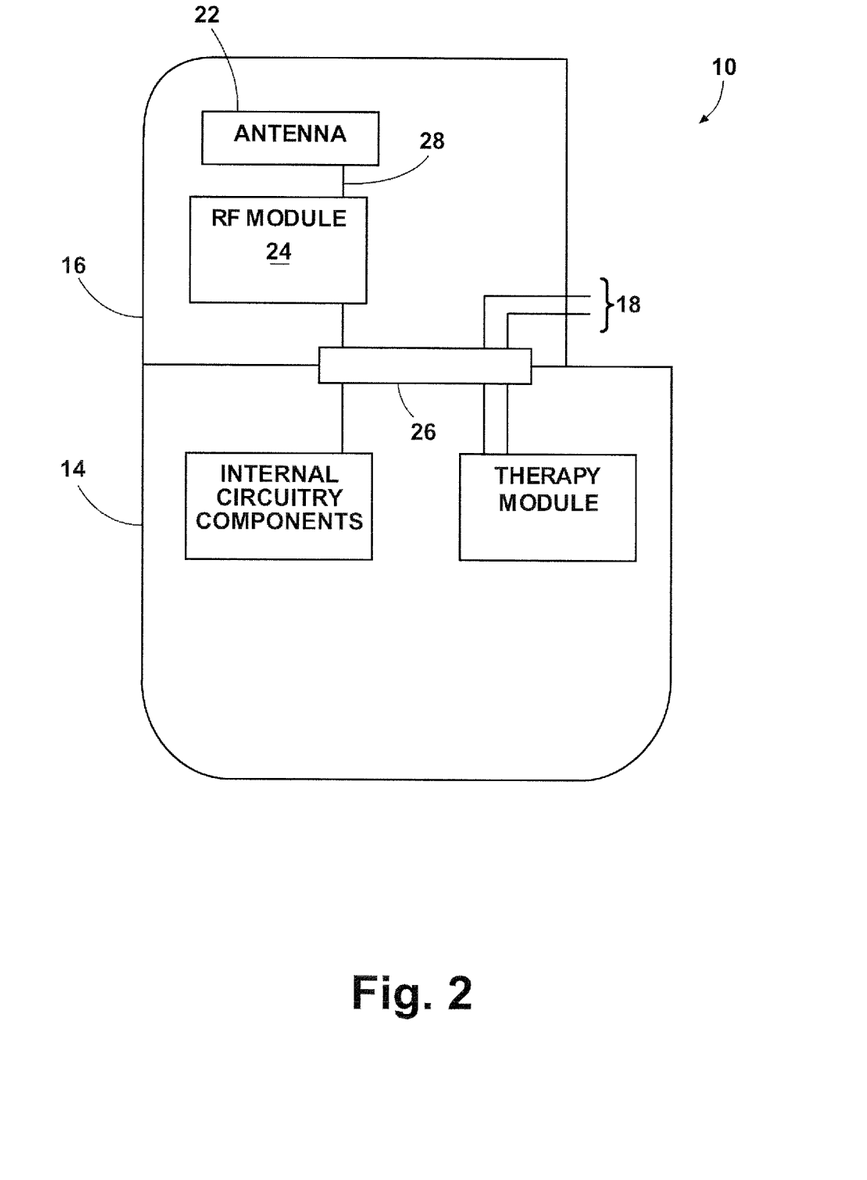
FIG. 2 is a schematic block diagram illustration of an exemplary implantable medical device in accordance with one or more embodiments of the present disclosure.

FIG. 2 is a simplified schematic representation of an IMD 10 and several functional elements associated therewith. IMD 10 generally includes hermetically sealed housing 14 and header block 16 coupled to housing 14, an antenna 22 arranged on an exterior of housing 14, and an RF module 24 arranged on an exterior of housing 14. IMD 10 includes one or more feedthrough conductive paths 26 extending through housing 14 for communicatively coupling the telemetry RF module 24 to at least one interior circuitry component within housing 14. In practice, IMD 10 will also include a number of conventional components and features necessary to support the functionality of IMD 10 as known in the art, such as a therapy module, a controller, a memory, a power supply, etc. Such conventional elements and the operation of these and other conventional elements will not be described herein.

Antenna 22 for IMD 10 is formed at a location exterior to housing 14 to allow for far field telemetry operations and minimize the reduction in radiation efficiencies that can be caused by the conductive housing 14. In one or more embodiments, antenna 22 is formed from a biocompatible conductive material, such as but not limited to at least one of the following materials: Platinum, Iridium, Platinum-Iridium alloys, Alumina, Silver, Gold, Palladium, Silver-Palladium or mixtures thereof, or Niobium, Molybdenum and/or Moly-manganese or other suitable materials.

Telemetry RF module 24 or other telemetry circuitry is further arranged at a location exterior to housing 14, such that both antenna 22 and RF module 24 are arranged on the exterior of housing 14. RF module 24 may include any number of components, including, without limitation: electrical devices, ICs, amplifiers, signal generators, a receiver and a transmitter (or a transceiver), modulators, microprocessors, controllers, memories, power supplies, and the like. RF module 24 may further include a matching circuit or a matching circuit may be positioned between RF module 24 and antenna 22. A matching circuit may include any number of components, including, without limitation: electrical components such as capacitors, resistors, or inductors; filters; baluns; tuning elements; varactors; limiter diodes; or the like, that are all suitably configured to provide impedance matching between antenna 22 and RF module 24, thus improving the efficiency of antenna 22. Briefly, RF module 24 supports RF telemetry communication for IMD 10, including, without limitation: generating RF transmit energy; providing RF transmit signals to antenna 22; processing RF telemetry signals received by antenna 22, and the like. For some applications, RF module 24 may be designed to leverage the conductive material used for housing 14 as an RF ground plane, and RF module 24 may be designed in accordance with the intended application of IMD 10, the electrical characteristics of the environment surrounding the implant location, the desired operating frequency range, the desired RF antenna range, and other practical considerations.

Antenna 22 is communicatively coupled to RF module 24 by an electrical interconnect 28 to facilitate RF telemetry between IMD 10 and an external device. Generally, antenna 22 is suitably configured for RF operation (e.g., UHF or VHF operation, 401 to 406 MHz for the MICS/MEDS bands, 900 MHz/2.4 GHz and other ISM bands, etc.). Antenna 22 may have characteristics resembling a monopole antenna, characteristics resembling a dipole antenna, characteristics resembling a coplanar waveguide antenna, characteristics resembling a stripline antenna, characteristics resembling a microstrip antenna, and/or characteristics resembling a transmission line antenna. Antenna 22 may also have any number of radiating elements, which may be driven by any number of distinct RF signal sources. In this regard, antenna 22 may have a plurality of radiating elements configured to provide spatial or polarization diversity.

In one or more embodiments, antenna 22 can thus be positioned at a location on exterior of the housing 14 and spaced apart a desired distance from housing 14 to achieve a desirable radiation efficiency. Housing 14 is typically formed from a conductive material that can limit the radiation efficiency of the IMD RF telemetry antenna 22, thereby serving to limit the data transfer distance for the antenna 22 for RF telemetry operations. Improved far field telemetry operations can be achieved by situating antenna 22 a desired distance away from the surface of housing 14.

Figure 3:
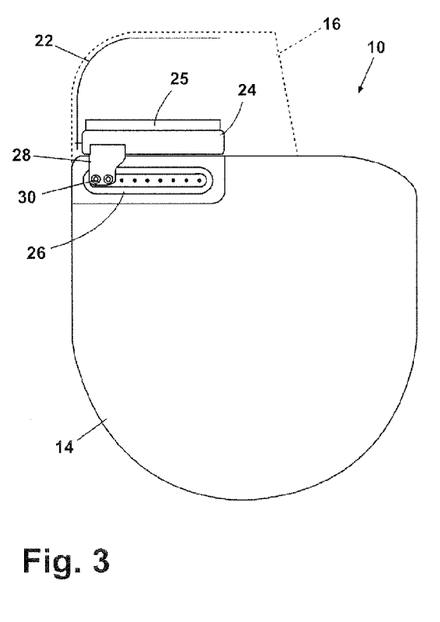
FIG. 3 is a side, partial cutaway view of an exemplary implantable medical device in accordance with one or more embodiments of the present disclosure.

Referring now to FIG. 3, a side view of an implantable medical device ("IMD") is illustrated in accordance with one or more embodiments in which external RF module 24 may comprise a self-contained RF module (e.g., RF circuitry and/or other digital circuitry is self-contained within an enclosed material). In some embodiments, self-contained RF module 24 may comprise a potted, printed circuit board (PCB) flex material, IC material, or other modular circuit material. In one or more embodiments, RF module 24 and antenna 22 are arranged within header block 16 on an exterior of housing 14. In some embodiments, either or both of RF module 24 and antenna 22 may be conformally shaped to an exterior surface of housing 14 or to the shape of header block 16. For example, referring to FIG. 3, antenna 22 is shown to conform to the shape of header 16. In this manner, antenna 22 may be shaped to extend away from housing 14 in order to situate antenna 22 a desired distance away from the surface of housing 14 for optimal radiating characteristics, shaped for other operation characteristics, or shaped to otherwise minimize the space it requires within header 16. Further, RF module 24 may be formed to abut an outer surface of housing 14 adjacent to feedthrough conductive paths 26. By way of further example of possible conformal shaping, referring to FIG. 4, RF module 24 can be formed of a flex PCB material and also conformally shaped to the shape of header block 16. Antenna 22 can be formed to extend adjacent to and along a length of RF module 24, such that both antenna 22 and RF module 24 are conformal to the shape of header 16. In some embodiments, antenna 22 can be etched on the perimeter of the flex RF module 24, and the end of antenna 22 can be formed to protrude away from RF module 24 for further improved antenna performance. In one or more embodiments, RF module 24 may be at least partially plated, coated or covered with a shielding material 25 for providing electromagnetic interference (EMI) and/or electromagnetic capability (EMC) isolation for the RF module 24.

Figure 4:
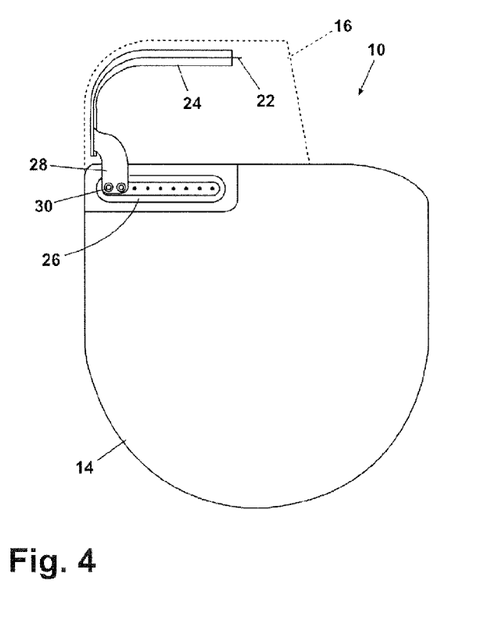
FIG. 4 is a side, partial cutaway view of another exemplary implantable medical device in accordance with one or more embodiments of the present disclosure.

In one or more embodiments, antenna 22 and RF module 24 may formed together in a single, unitary subassembly element. This would provide modularity for the antenna 22/RF module 24 subassembly element to allow it to be interchangeably utilized in a variety of possible combinations of headers 16 and housings 14. In this manner, depending upon the particular housing 14 to which the antenna 22/RF module 24 subassembly element would be connected, an appropriate header 16 could be selected to suit the environment surrounding IMD 10. In some embodiments, such an antenna 22/RF module 24 subassembly element could be formed by encasing the components within a potting material into a single conformal element, where such an arrangement advantageously provides a controlled thickness for the potting material, thereby providing known parasitics for both the circuitry of RF module 24 and for antenna 22. The potted antenna 22/RF module 24 subassembly element with known parasitics could be positioned within a header 16 or alternatively at a location exterior to the header 16.

In one or more embodiments, one or more feedthrough conductive paths 26 extend through housing 14 to communicatively couple RF module 24 to at least one component situated within housing 14. In some embodiments, an electrical interconnect 28 (e.g., ribbon wire connector or other wired connection) connects RF module 24 to feedthrough pins 30 in the feedthrough conductive paths 26 (e.g, via welding), where a biocompatible medical adhesive or epoxy may be used to cover and electrically insulate any exposed portions of the feedthrough pin 30 or other portions of feedthrough conductive paths 26. Feedthrough conductive paths 26 may be located at any location on housing 14, such that different possible antenna 22 and RF module 24 arrangements may be modified to accommodate different locations for the RF feedthrough conductive paths 26. Furthermore, depending upon the specific configuration and topology of antenna 22 and RF module 24, a single feedthrough conductive path 26 may provide insulated routing for any number of separate radiating elements, and/or IMD 10 may include any number of separate feedthrough conductive paths 26 for a like number of separate antenna elements. Conventional IMDs have traditionally had unfiltered RF feedthroughs connecting external antennas to internal RF telemetry circuitry, which has provided an open pathway for destructive EMI signals to enter into the interior of the IMD housing and negatively impact the operation of circuitry contained therein. For example, patients are often precluded from obtaining MRI's due to such destructive EMI signals. By situating RF module 24 on the exterior of housing 14, signal processing of telemetry signals received by and transmitted from antenna 22 can be performed by RF module 24 on the exterior of housing 14. In this manner, the signals that are communicated across feedthrough conductive paths 26 can be limited to power signals for RF module 24 from a power source within housing 14 and/or low frequency data bit signals corresponding to information contained within radio frequency (RF) telemetry signals that are received by and transmitted from antenna 22. This allows the feedthrough conductive path 26 to be filtered to prevent undesired interference signals (e.g., electromagnetic interference (EMI) signals, magnetic resonance imaging (MRI) signals, noise, etc.) from entering housing 14 through the feedthrough conductive path 26 coupled to RF module 24. In conventional IMDs in which RF telemetry modules or circuitry are located within the IMD housing, the RF feedthroughs cannot typically be filtered without filtering out the telemetry signals themselves.

The present improved configuration of positioning the RF module 24 on an exterior of housing 14 allows only low frequency data bit signals to be required to be communicated across the feedthrough conductive path 26, thereby allowing the feedthrough conductive path 26 to contain filter devices (not shown) to prevent the passage of EMI signals and other unwanted signals into the interior of housing 14 of IMD 10. Further, such filtered feedthrough conductive paths 26 may provide a higher level of PC-69 protection, which is the standard developed by the Association for the Advancement of Medical Instrumentation's (AAMI) EMC working group (AAMI PC69: Active implantable medical devices-Electromagnetic compatibility-EMC test protocols for implantable cardiac pacemakers and implantable cardioverter defibrillators) that sets forth electromagnetic compatibility test protocols for implantable pulse generators (IPGs) and implantable cardioverter defibrillators (ICDs). The PC-69 standard contains test requirements and procedures for testing such devices for electrical interference in frequency bands of 450 MHz to 3,000 MHz. Still further, such filtered feedthrough conductive paths 26 may provide higher levels of ESD protection as well. Even further, by locating RF module 24 on the exterior of housing 14, interference that the RF module 24 itself can cause on other internal circuitry (e.g., therapy modules or pulsing circuits) situated within housing 14 can be avoided while further preventing such other internal circuitry within housing 14 from interfering with and reducing the performance of RF module 24.

Figure 5:
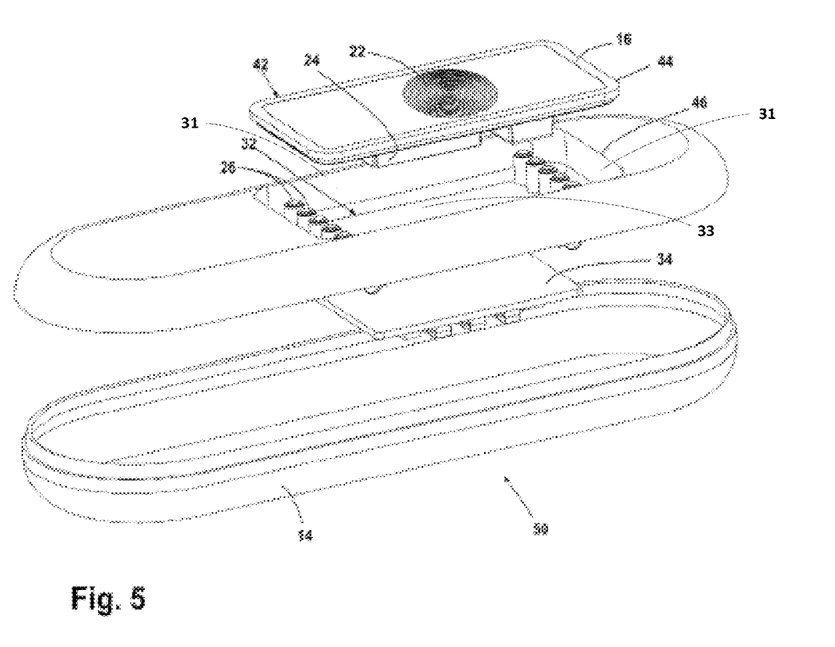
FIG. 5 is an exploded perspective view of an exemplary implantable medical device in accordance with one or more embodiments of the present disclosure.
Figure 6:
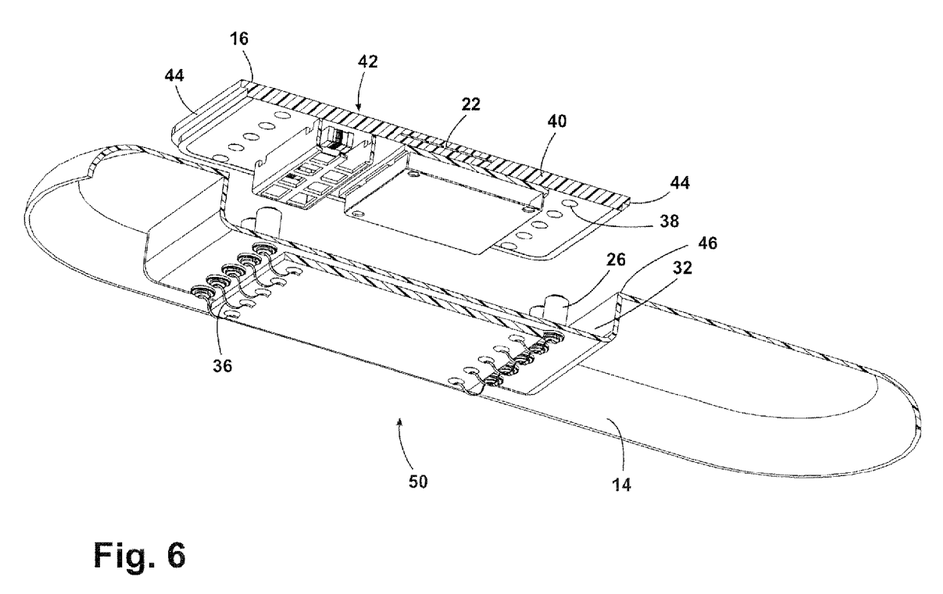
FIG. 6 is an exploded, perspective, partial cutaway view of an exemplary implantable medical device in accordance with one or more embodiments of the present disclosure.
Figure 7:
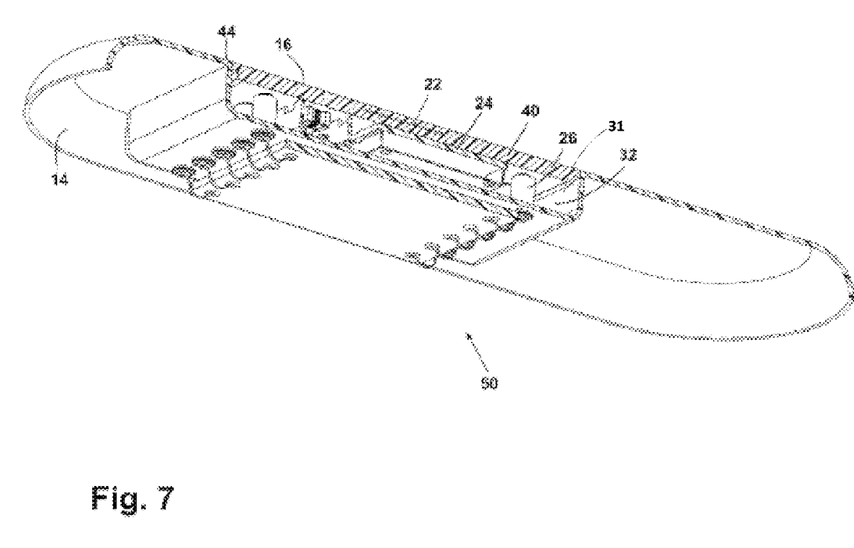
FIG. 7 is a perspective, partial cutaway view of an exemplary implantable medical device in accordance with one or more embodiments of the present disclosure.

Referring now to FIGS. 5-7, a separate integrated antenna and telemetry module assembly 42 formed in accordance with one or more embodiments is illustrated containing an embedded antenna 22, wherein the integrated antenna and telemetry module assembly 42 may be attached to an exterior surface 46 of a housing 14 for IMD 50. It is noted that similarly numbered components of IMD 50 will function substantially identical to such numbered components of IMD 10 and a description of their operation will not be repeated for ease of description. In one or more embodiments, a recessed region or shelf region 32 may be formed within a portion of the exterior surface 46 of housing 14, as illustrated in the exploded view of IMD 50 in FIG. 5. The recessed region 32 may include one or more side surfaces 31 and a bottom surface 33. In one or more embodiments, RF module 24 may be attached to one side of integrated antenna and telemetry module assembly 42. Integrated assembly 42 may be arranged such that RF module 24 is received within recessed region 32 when integrated assembly 42 is attached to exterior 46 of housing 14. The integrated assembly 42 includes side surfaces 44 which may be arranged to engage exterior surface 46 of housing 14 when integrated assembly 42 is situated within recessed region 32. In other embodiments, as depicted in FIG. 7, integrated assembly 42 side surfaces 44 may also be arranged to engage side-surfaces 31 of recessed region 32. In some embodiments, a hermetic cover 16 may be positioned over the exposed surface of integrated assembly 42, where hermetic cover 16 may comprise a separate header block similar to header block 16 or may comprise part of the integrated assembly 42 itself (e.g., a biocompatible layer that is arranged as the outermost surface layer of integrated assembly 42).

With further reference to FIG. 6, filtered feedthrough conductive paths 26 may be positioned within recessed region 32 so as to engage conductive pads 38 formed on a bottom surface of integrated assembly 42 is positioned over recessed region 32 and attached to housing 14. Conductive pads 38 are communicatively coupled to RF module 24. Internal circuitry and other components contained within the interior of housing 14, such as on PWB 34, may be communicatively coupled to filtered feedthrough conductive paths 26 through wired connectors 36 on the interior of the housing 14. In one or more embodiments, integrated assembly 42 may include a ceramic material 40, PWB material or another substrate material that is formed around antenna 22 so as to embed antenna 22 within ceramic material 40. RF module 24 may then be attached to the bottom surface of ceramic material 40. In one or more embodiments, ceramic material 40 and antenna 22 may be cofired together into a monolithic structure to which RF module 24 is attached to form the integrated assembly 42. Referring to the partial cutaway view of FIG. 7, the edges 44 of integrated assembly 42 may then be hermetically sealed to the exterior surface 46 of housing 14 by laser welding or other suitable bonding techniques that will provide a hermetic seal without damaging the internal components of the integrated assembly 42, as known to those skilled in the art. As used herein, integrated assembly 42 may then perform the function of hermetic cover or header 16.

In one or more embodiments, the use of recessed region 32 allows RF module 24 to be received within recessed region 32 such that integrated assembly 42 can be positioned to be substantially flush with the exterior surface of housing 14 in order to reduce the overall dimensions of IMD 50 and provide a smoothly contoured shape of IMD 50 suitable for implantation on space-limited locations in a patient.

In one or more embodiments, the use of a cofired ceramic material 40 allows integrated assembly 42 to be a specially designed and shaped hermetic cover for desired characteristics of IMD 10. In one aspect, the use of a cofired ceramic material allows integrated assembly 42 to specially formed or shaped to provide a desired passage of RF energy that is either radiated or received by telemetry antenna 22 encapsulated within integrated assembly 42. In one or more embodiments, the cofired ceramic material 40 for integrated assembly 42 comprises a high temperature co-fire ceramic (HTCC) material having a melting point between about 1100 C.° and 1700 C.°, wherein layers of the ceramic material 40 and antenna 22 are cofired together at such temperatures to form the monolithic structure for integrated assembly 42. In one or more embodiments, the cofired ceramic material 40 comprises a low temperature co-fired ceramic (LTCC) material having melting point between about 850 C.° and 1150 C.°. Methods for co-firing layers of ceramic materials together to form monolithic structures for use in IMDs are described, for example, in U.S. Pat. No. 6,414,835 and U.S. Pat. No. 7,164,572, the contents of both of which are hereby incorporated by reference in their entireties.

According to one or more embodiments, the use of a co-firing technique to form a integrated assembly 42 that includes the embedded antenna 22 and is attached to the exterior of housing 14 allows for the manufacture of low-cost, miniaturized, hermetically sealed antenna structures suitable for implantation within tissue and/or in direct or indirect contact with diverse body fluids. Further, the ceramic materials used to form integrated assembly 42 can be loaded with powders of a desired dielectric constant so as to produce a structure having a desired effective dielectric value that is situated between antenna 22 and the surrounding environment.

In one or more embodiments, the ceramic integrated assembly 42 can be formed from one or more layers or sheets of materials (or segments of tape) that comprise the ceramic material 40, antenna 22 and electrical interconnects may be printed with a metalized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metalized paste) vaporizes and/or is incinerated while the remaining material fuses or sinters. In some embodiments, the materials suitable for use as cofireable conductors for forming the antenna 22 are biocompatible metal materials described herein or other materials suitable for the metalized paste, In one or more embodiments, the stacked laminates are then co-fired together at temperatures between about 850 C.° and 1150 C.° for LTCC materials and between about 1100 C.° and 1700 C.° for HTCC materials to form the ceramic integrated assembly 42 having the embedded antenna 22. In some embodiments, the materials suitable for use as cofireable ceramics include alumina ($Al_2O_3$), aluminum nitride, beryllium oxide, Silica ($SiO_2$), Zirconia ($ZrO_2$), glass-ceramic materials, glass suspended in an organic (polymer) binder, or mixtures thereof.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An implantable medical device ("IMD"), comprising:
   a hermetic housing having an exterior surface that defines a recessed region having a plurality of side surfaces and a bottom surface, wherein the hermetic housing further comprises at least one filtered feedthrough conductive path through the bottom surface of the recessed region; and
   an integrated antenna and telemetry module assembly, wherein the integrated antenna and telemetry module assembly comprises:
      a hermetic cover that comprises ceramic;
      an antenna embedded within the ceramic of the hermetic cover; and
      a telemetry module attached to the hermetic cover and communicatively coupled with the antenna;
   wherein the recessed region is configured to receive the integrated antenna and telemetry module such that the hermetic cover is sealed against the plurality of side surfaces of the recessed region of the hermetic housing, and the telemetry module is enclosed within the recessed region and covered by the hermetic cover when the hermetic cover is sealed against the plurality of side surfaces of the recessed region of the hermetic housing; and
   wherein the at least one filtered feedthrough conductive path extending through the bottom surface of the recessed region communicatively couples the telemetry module to at least one component within the housing.

2. The implantable medical device of claim 1, wherein the telemetry module is conformally shaped to the recessed region of the hermetic housing.

3. The implantable medical device of claim 1, wherein the at least one filtered feedthrough conductive path prevents undesired interference signals from entering the hermetic housing through the filtered feedthrough conductive path coupled to the telemetry module.

4. The implantable medical device of claim 1, wherein the ceramic material and antenna are cofired together into a monolithic structure.

5. The implantable medical device of claim 1, wherein the telemetry module comprises a shielding layer for providing at least one of electromagnetic interference (EMI) and electromagnetic capability (EMC) isolation for the telemetry module.

6. The implantable medical device of claim 1, wherein the telemetry module is a potted external flex radio frequency (RF) module having self-contained RF circuitry and digital circuitry.

7. The implantable medical device of claim 6, wherein a telemetry module and the antenna are integrated together in the potted external flex radio frequency (RF) module.

8. The implantable medical device of claim 1, wherein the IMD further comprises a header coupled to the housing.

* * * * *